(12) United States Patent
Ootsubo (10) Patent No.: US 8,460,287 B2
(45) Date of Patent: Jun. 11, 2013

(54) PFO CLOSING DEVICE

(75) Inventor: Seiichi Ootsubo, Hadano (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 986 days.

(21) Appl. No.: 12/200,505

(22) Filed: Aug. 28, 2008

(65) Prior Publication Data
US 2009/0069809 A1 Mar. 12, 2009

Related U.S. Application Data

(60) Provisional application No. 60/976,076, filed on Sep. 28, 2007.

(30) Foreign Application Priority Data

Aug. 28, 2007 (JP) .................................. 2007-221904

(51) Int. Cl.
*A61B 18/18* (2006.01)
*A61B 17/08* (2006.01)
*A61D 1/00* (2006.01)
*A61N 1/00* (2006.01)

(52) U.S. Cl.
USPC .............. 606/41; 606/213; 607/116; 607/122

(58) Field of Classification Search
USPC .............. 606/27–52, 213–215; 607/101, 102, 607/122, 116
See application file for complete search history.

(56) References Cited

U.S. PATENT DOCUMENTS

| | | | |
|---|---|---|---|
| 5,507,744 A | 4/1996 | Tay et al. | |
| 5,709,224 A | 1/1998 | Behl et al. | |
| 5,810,810 A | 9/1998 | Tay et al. | |
| 5,827,268 A | 10/1998 | Laufer | |
| 5,919,200 A | 7/1999 | Stambaugh et al. | |
| 6,004,316 A | 12/1999 | Laufer | |
| 6,063,085 A | 5/2000 | Tay et al. | |
| 6,077,261 A | 6/2000 | Behl et al. | |
| 6,629,534 B1 | 10/2003 | St. Goar et al. | |
| 6,752,813 B2 | 6/2004 | Goldfarb et al. | |
| 6,939,348 B2 | 9/2005 | Malecki et al. | |
| 7,165,552 B2 | 1/2007 | Deem et al. | |
| 7,186,251 B2 | 3/2007 | Malecki et al. | |
| 7,226,467 B2 | 6/2007 | Lucatero et al. | |

(Continued)

FOREIGN PATENT DOCUMENTS

| WO | WO 2007/100067 A1 | 9/2007 |
|---|---|---|
| WO | WO 2008/073727 A1 | 6/2008 |

*Primary Examiner* — Matthew F Desanto
(74) *Attorney, Agent, or Firm* — Buchanan Ingersoll & Rooney PC (57) ABSTRACT

A PFO closing device includes: a clamper including a stick portion provided at a distal portion of a catheter for sticking to a foramen ovale valve and a sandwich member for sandwiching a biological tissue composed of the foramen ovale valve and an atrial septum secundum in cooperation with the stick portion; a cautery device including at least one electrode portion to be inserted into the foramen ovale between the foramen ovale valve and the atrial septum secundum; and an electric energy supply unit for supplying electric energy to the electrode portion, wherein the electrode portion is inserted into the foramen ovale and at the same time, the foramen ovale valve and the atrial septum secundum are sandwiched by the clamper, electric energy is supplied from the electric energy supply unit to the electrode portion and the foramen ovale valve and the atrial septum secundum are mutually fused.

13 Claims, 8 Drawing Sheets

U.S. PATENT DOCUMENTS

| | | |
|---|---|---|
| 7,257,450 B2 | 8/2007 | Auth et al. |
| 7,293,562 B2 | 11/2007 | Malecki et al. |
| 7,311,701 B2 | 12/2007 | Gifford et al. |
| 7,797,056 B2 * | 9/2010 | Forde et al. .................. 607/116 |
| 8,021,359 B2 * | 9/2011 | Auth et al. ..................... 606/28 |
| 8,172,839 B2 * | 5/2012 | Kato ............................... 606/50 |
| 2004/0003819 A1 | 1/2004 | St. Goar et al. |
| 2004/0030382 A1 | 2/2004 | St. Goar et al. |
| 2004/0039442 A1 | 2/2004 | St. Goar et al. |
| 2004/0044350 A1 | 3/2004 | Martin et al. |
| 2004/0049207 A1 | 3/2004 | Goldfarb et al. |
| 2004/0092962 A1 | 5/2004 | Thornton et al. |
| 2004/0225300 A1 | 11/2004 | Goldfarb et al. |
| 2004/0230185 A1 | 11/2004 | Malecki et al. |
| 2004/0243122 A1 | 12/2004 | Auth et al. |
| 2004/0267191 A1 | 12/2004 | Gifford, III et al. |
| 2005/0021056 A1 | 1/2005 | St. Goar et al. |
| 2005/0021057 A1 | 1/2005 | St. Goar et al. |
| 2005/0033288 A1 | 2/2005 | Auth et al. |
| 2005/0033446 A1 | 2/2005 | Deem et al. |
| 2005/0080406 A1 | 4/2005 | Malecki et al. |
| 2005/0131401 A1 | 6/2005 | Malecki et al. |
| 2005/0131460 A1 | 6/2005 | Gifford, III et al. |
| 2005/0192626 A1 | 9/2005 | Widomski et al. |
| 2005/0192654 A1 | 9/2005 | Chanduszko et al. |
| 2005/0209636 A1 | 9/2005 | Widomski et al. |
| 2005/0216054 A1 | 9/2005 | Widomski et al. |
| 2006/0020275 A1 | 1/2006 | Goldfarb et al. |
| 2006/0027241 A1 | 2/2006 | Malecki et al. |
| 2006/0074410 A1 | 4/2006 | Malecki et al. |
| 2006/0241581 A1 | 10/2006 | Malecki et al. |
| 2006/0241582 A1 | 10/2006 | Malecki et al. |
| 2006/0241583 A1 | 10/2006 | Malecki et al. |
| 2006/0241584 A1 | 10/2006 | Malecki et al. |
| 2006/0247612 A1 | 11/2006 | Malecki et al. |
| 2006/0271030 A1 * | 11/2006 | Francis et al. .................. 606/27 |
| 2006/0271040 A1 | 11/2006 | Horne et al. |
| 2006/0271089 A1 | 11/2006 | Alejandro et al. |
| 2006/0276779 A1 | 12/2006 | Malecki et al. |
| 2006/0276846 A1 | 12/2006 | Malecki et al. |
| 2007/0010806 A1 | 1/2007 | Malecki et al. |
| 2007/0027445 A1 | 2/2007 | Gifford et al. |
| 2007/0038293 A1 | 2/2007 | St.Goar et al. |
| 2007/0044811 A1 | 3/2007 | Deem et al. |
| 2007/0078485 A1 | 4/2007 | Deem et al. |
| 2007/0088355 A9 | 4/2007 | Auth et al. |
| 2007/0093804 A1 | 4/2007 | Kaveckis et al. |
| 2007/0093805 A1 | 4/2007 | Auth et al. |
| 2007/0100324 A1 | 5/2007 | Tempel et al. |
| 2007/0100356 A1 | 5/2007 | Lucatero et al. |
| 2007/0106214 A1 | 5/2007 | Gray et al. |
| 2007/0112347 A1 | 5/2007 | Malecki et al. |
| 2007/0118155 A1 | 5/2007 | Goldfarb et al. |
| 2007/0123824 A1 | 5/2007 | Kaveckis |
| 2007/0123851 A1 | 5/2007 | Alejandro et al. |
| 2007/0123852 A1 | 5/2007 | Deem et al. |
| 2007/0129737 A1 | 6/2007 | Goldfarb et al. |
| 2007/0203479 A1 | 8/2007 | Auth et al. |
| 2007/0287999 A1 | 12/2007 | Malecki et al. |
| 2007/0299434 A1 | 12/2007 | Malecki et al. |
| 2008/0004658 A1 | 1/2008 | Malecki et al. |
| 2008/0009859 A1 | 1/2008 | Auth et al. |
| 2008/0045937 A1 * | 2/2008 | Whisenant et al. ............. 606/33 |
| 2008/0051703 A1 | 2/2008 | Thornton et al. |
| 2008/0051807 A1 | 2/2008 | St. Goar et al. |
| 2008/0058683 A1 | 3/2008 | Gifford et al. |
| 2008/0097489 A1 | 4/2008 | Goldfarb et al. |
| 2008/0140064 A1 | 6/2008 | Vegesna |
| 2008/0140068 A1 | 6/2008 | Taimisto |
| 2008/0140069 A1 | 6/2008 | Filloux et al. |
| 2008/0140070 A1 | 6/2008 | Filloux et al. |
| 2008/0140071 A1 | 6/2008 | Vegesna |
| 2008/0140074 A1 | 6/2008 | Horne et al. |
| 2008/0140112 A1 | 6/2008 | Horne |
| 2008/0140113 A1 | 6/2008 | Taimisto |
| 2008/0140170 A1 | 6/2008 | Filloux et al. |
| 2009/0069810 A1 | 3/2009 | Kuroda et al. |

\* cited by examiner

PFO CLOSING DEVICE

This application is based on and claims priority under 35 U.S.C. §119(e) with respect to U.S. Application No. 60/976,076 filed on Sep. 28, 2007, the entire content of which is incorporated herein by reference. This application is also based on and claims priority under 35 U.S.C. §119(a) with respect to Japanese Patent Application 2007-221904 filed Aug. 28, 2007, the entire content of which is hereby incorporated by reference.

TECHNOLOGICAL FIELD

The present invention generally relates to a biological tissue closing device. more specifically, the invention pertains to a PFO closing device which closes a defect occurring in a living body.

BACKGROUND DISCUSSION

Recently, a patent foramen ovale (hereinafter, referred as to PFO: Patent Foramen Ovale) has been cited as a cardiogenic factor in strokes and migraines. A PFO is a medical condition in which a foramen ovale which makes blood shunt for the right to the left in the heart of a baby or young child remains even after the young child becomes an adult. It is said that 20 to 30% of adults possess it.

The foramen ovale occurs at a septum secundum (Septum Secundum, hereinafter, referred to as atrial septum secundum) of the heart and the pressure on the left atrium side exceeds the pressure on the right atrium side in the heart on a normal occasion, so that it is occluded by a septum primum (Septum Primum, hereinafter, referred to as foramen ovale valve), but when the pressure on the right atrium side exceeds the pressure on the left atrium side on the occasion of a strain (for example, when coughing, when holding on) or the like, the foramen ovale valve opens to the left atrium side and it happens that blood flows from the right atrium side (venous side) into the left atrium side (arterial side). When a thrombus is included in this blood, the thrombus is shifted from the venous side to the arterial side, flows in a route of left atrium→left ventricle→aorta→brain, and becomes a factor in strokes, migraines or the like.

Treatments for such a condition include a treatment by a percutaneous catheter procedure. This is considered to be a desirable method if the same effect as an open heart surgery can be obtained.

A device of a closing technique using the percutaneous catheter can be used also in case of closing defects such as a congenital atrial septal defect indwelled (ASD), a PFO, a ventricular septal defect (VSD) and a patent ductus arteriosus (PDA). In the past, the device which has been used is a device which sandwiches the foramen ovale valve and the atrial septum secundum by using disk-shaped membranes or anchor members for closing the defect and these are indwelled in the body.

The membranes or anchor members are foreign substances for a human body and moreover, it is easy for a thrombus to be attached. In particular, when a thrombus is attached on a disk-shaped membrane or the like on the left atrium side, this flows and there is a possibility that it becomes a cause of a stroke, and there is also a fear that a foramen ovale valve of a thin wall thickness is broken. In addition, these members are not position-fixed in a state of being sandwiched and there is also a possibility of causing a positional displacement.

Consequently, recently, there has been proposed a PFO closing device which is described in WO2004/086944 A2 (see summary, FIG. 10 and the like). This PFO closing device is a device in which an apparatus is inserted into the foramen ovale from the right atrium toward the left atrium, a foramen ovale valve is pulled to the foramen ovale so as to close it and the tissue is fused by applying electric energy. However, the foramen ovale, the foramen ovale valve and the atrial septum secundum are different not only terms of sizes but also in a condition of thicknesses, shapes or the like depending on the individual and according to circumstances, the size or the like of the apparatus is restricted a lot. Also, on occasion when the procedure is performed, there is a fear that it becomes difficult to pull various forms of foramen ovale valves to the foramen ovale at anytime and certainly.

Consequently, as shown in Japanese Patent Application No. 2006-47636 (see summary, FIG. 10 and the like), the present patent applicant proposed previously a PFO closing device in which the foramen ovale valve and the atrial septum secundum are sandwiched by a pair of electrodes and the tissue is fused by applying electric energy from both the electrodes. This PFO closing device uses a clamper in which a stick portion and a sandwich member are composed of a pair of electrodes and with respect to one of them, the stick portion composed of a needle electrode is stuck into the foramen ovale valve and thereafter, the foramen ovale valve and the atrial septum secundum are sandwiched with respect to the sandwich member which is the other electrode, the biological tissue is applied with electric energy, and the fusion is carried out. If this PFO closing device is used, foreign substances are not indwelled in the body, the construction is relatively simple, also the procedure becomes relatively easy and the foramen ovale valve and the atrial septum secundum can be fused certainly.

However, in this device, the clamper is configured to be the electrodes, so that when electric energy is applied and in case of an example in which the atrial septum secundum is thick, the distance between the aimed fusion region and the electrodes is relatively far and there is a possibility that damage will occur to a region which is not intended to be fused.

Also, depending on the inter-individual difference of the thickness of a biological tissue, fluctuation occurs on the distance between the fusion region and the electrode and also there is a possibility that fluctuation will occur on the fusion force.

SUMMARY

A PFO closing device disclosed here includes: a clamper including a stick portion provided at a distal portion of a catheter for sticking to a foramen ovale valve and a sandwich member for sandwiching a biological tissue composed of the foramen ovale valve and an atrial septum secundum in cooperation with the stick portion; a cautery device including at least one electrode portion to be inserted into the foramen ovale between the foramen ovale valve and the atrial septum secundum; and an electric energy supply unit for supplying electric energy to the electrode portion, wherein the electrode portion is inserted into the foramen ovale and at the same time, the foramen ovale valve and the atrial septum secundum are sandwiched by the clamper, electric energy is supplied from the electric energy supply unit to the electrode portion and the foramen ovale valve and the atrial septum secundum are mutually fused.

The electrode portion is inserted into the foramen ovale and at the same time, the foramen ovale valve and the atrial septum secundum are sandwiched by the clamper, electric energy is supplied from the electric energy supply unit to the electrode portion and the foramen ovale valve and the atrial septum secundum are fused mutually, thus the electrode portion is positioned on fusion surface, so that it is possible to input electric energy efficiently and it is possible to suppress damage to the biological tissue at the minimum. Also, the electrode portion is positioned on the fusion surface, so that the fusion force does not depend on the thickness of the foramen ovale valve and the atrial septum secundum which are sandwiched by the clamper and it is possible to repress fluctuation of the fusion force as small as possible.

In particular, if the electrode portion includes two poles, energization is executed between the electrode portions which are positioned on the fusion surface, so that it is possible to input electric energy efficiently, suppress damage to the biological tissue to a minimum and also repress fluctuation of the fusion force as small as possible.

If the electrode portion is an active electrode and a pole which becomes a counterpart with respect to the electrode portion is provided at the stick portion, at the sandwich member or on the outside of the body, the electrode portion is positioned at the fusion surface, so that it is possible to input electric energy efficiently and it is possible to suppress damage to the biological tissue as small as possible.

The distal portion of a guiding catheter for guiding the catheter is preferably bent to guide and insert the catheter into the foramen ovale between the foramen ovale valve and the atrial septum secundum. Without significant regard to the state of the foramen ovale valve and the atrial septum secundum which differ depending on the person, it is possible to deal therewith more easily than a case of a straight shape, and safety, convenience and speediness of the procedure are improved.

The proximal portion of the catheter can be provided with one operation unit for operating the clamper and the cautery device, and another operation member which is inserted into the catheter is provided for coupling the one operation unit with the clamper and the cautery device. The clamper and the cautery device can thus be operated simply by the operation of the operation unit without moving the whole catheter forward and backward. The operation of inserting the electrode portion and the operation of sticking or sandwiching can be performed more easily and also accurately and it is also possible to execute the insertion, sticking or sandwiching operation by a so-called single handed operation if desired, and so the operability is improved.

According to another aspect, a PFO closing device comprises a catheter and a clamper comprised of a needle portion disposed at the distal portion of the catheter for piercing a foramen ovale valve and a sandwich member positioned at the distal portion of the catheter, wherein the sandwich member and the needle portion together cooperate with one another to sandwich therebetween biological tissue composed of the foramen ovale valve and an atrial septum secundum. Two electrodes are movably positioned in the distal portion of the catheter to project distally beyond a distal end of the catheter, with the two electrodes being positionable in the foramen ovale between the foramen ovale valve and the atrial septum secundum. An electric energy supply unit is connected to the two electrodes to supply electric energy to the two electrodes. The electrodes are insertable into the foramen ovale while the foramen ovale valve and the atrial septum secundum are at the same time sandwiched by the clamper, whereupon electric energy supplied from the electric energy supply unit to the electrodes effects mutual fusing of the foramen ovale valve and the atrial septum secundum.

A method of closing a patent foramen ovale by bringing an atrial septum secundum and a foramen ovale valve into contact with each other and joining them together comprises introducing a clamper into an atrium of a heart, wherein the clamper comprising a needle part, puncturing the foramen ovale valve with the needle part, positioning at least one electrode of a cautery device between the atrial septum secundum and the foramen ovale valve, clamping tissue of the atrial septum secundum and the foramen ovale valve with the clamping part while the at least one electrode is positioned between the atrial septum secundum and the foramen ovale valve, and applying energy to the at least one electrode positioned between the atrial septum secundum and the foramen ovale valve to join together the atrial septum secundum and the foramen ovale valve.

BRIEF DESCRIPTION OF THE DRAWINGS

FIGS. 9(A) and (B) are perspective views showing another example of a positioning hold mechanism, in which FIG. 9A shows a state before deformation and FIG. 9B shows a state after deformation.

DETAILED DESCRIPTION

FIGS. 1-4 illustrate aspects of a PFO closing device according to one disclosed embodiment. It should be noted in FIG. 2 that the operation unit 70 is described and illustrated in a state of being demagnified because of space limitations.

Figure 1:
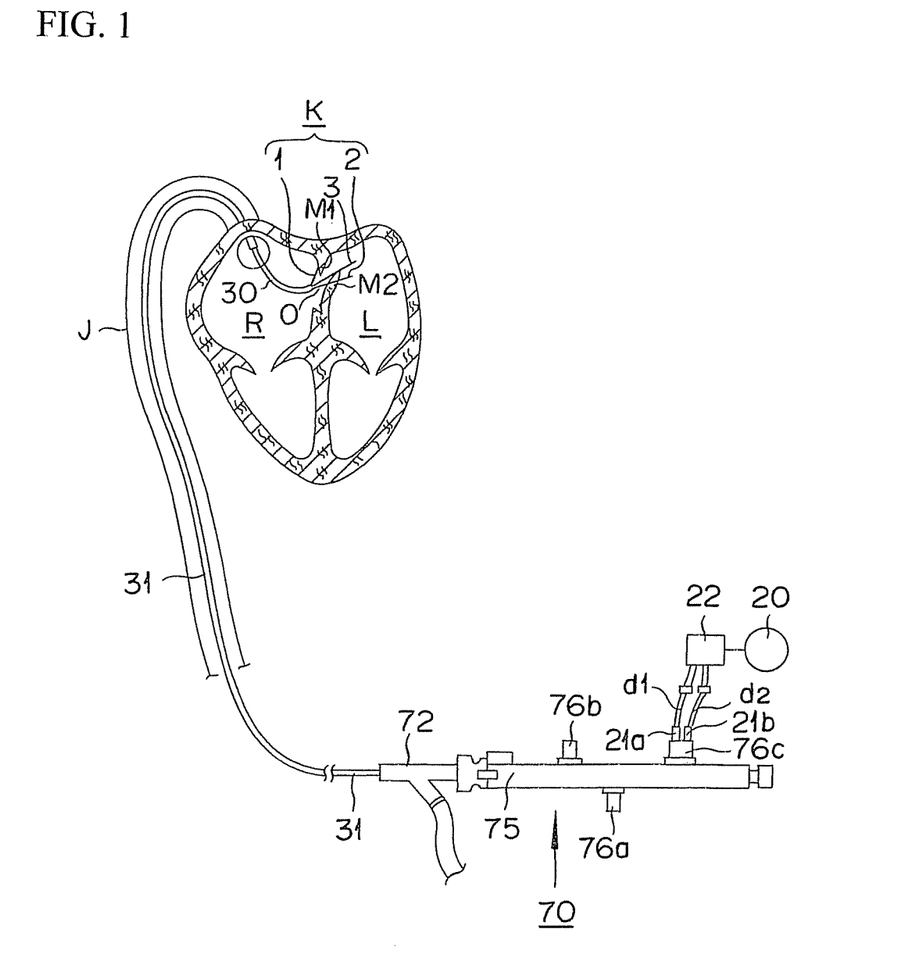
FIG. 1 is a schematic cross-section view showing a PFO closing device as disclosed here.

A PFO closing device according to one embodiment includes, as shown in FIG. 1, a clamper K for sandwiching a foramen ovale valve M2 and an atrial septum secundum M1; an energy supply unit 20 for supplying energy by which a biological tissue M (general term of M1, M2) of a portion sandwiched by the clamper K is welded and fused; and a cautery device 3 for welding and fusing a biological tissue M (general term of M1, M2) by energy supplied from the energy supply unit 20, wherein the clamper K and the cautery device 3 are positioned in a percutaneous catheter 30 from a distal tip thereof so as to be capable of protruding from the distal tip of the catheter while also being backward-movable.

This device, when used, is first inserted, for example, from a femoral venous J in a state in which there is housed in a guiding catheter 31 the whole of the clamper K and the cautery device 3 which are provided at the distal tip of the catheter 30. If the distal tip reaches the region of the heart at which the procedure is executed, the clamper K and the cautery device 3 are operated to protrude from the distal tip of the guiding catheter 31, the cautery device 3 is inserted into a defect O of the foramen ovale (hereinafter sometimes simply referred to as foramen ovale O) and the tissues of the atrial septum secundum M1 and the foramen ovale valve M2 of the heart having the defect O of the foramen ovale are sandwiched by the clamper K. In this sandwiched state, the cautery device 3 is supplied with electric energy, both the tissues are welded and fused and the defect O is closed. It should be noted in the drawing that L denotes a left atrium and R denotes a right atrium.

Figure 2:
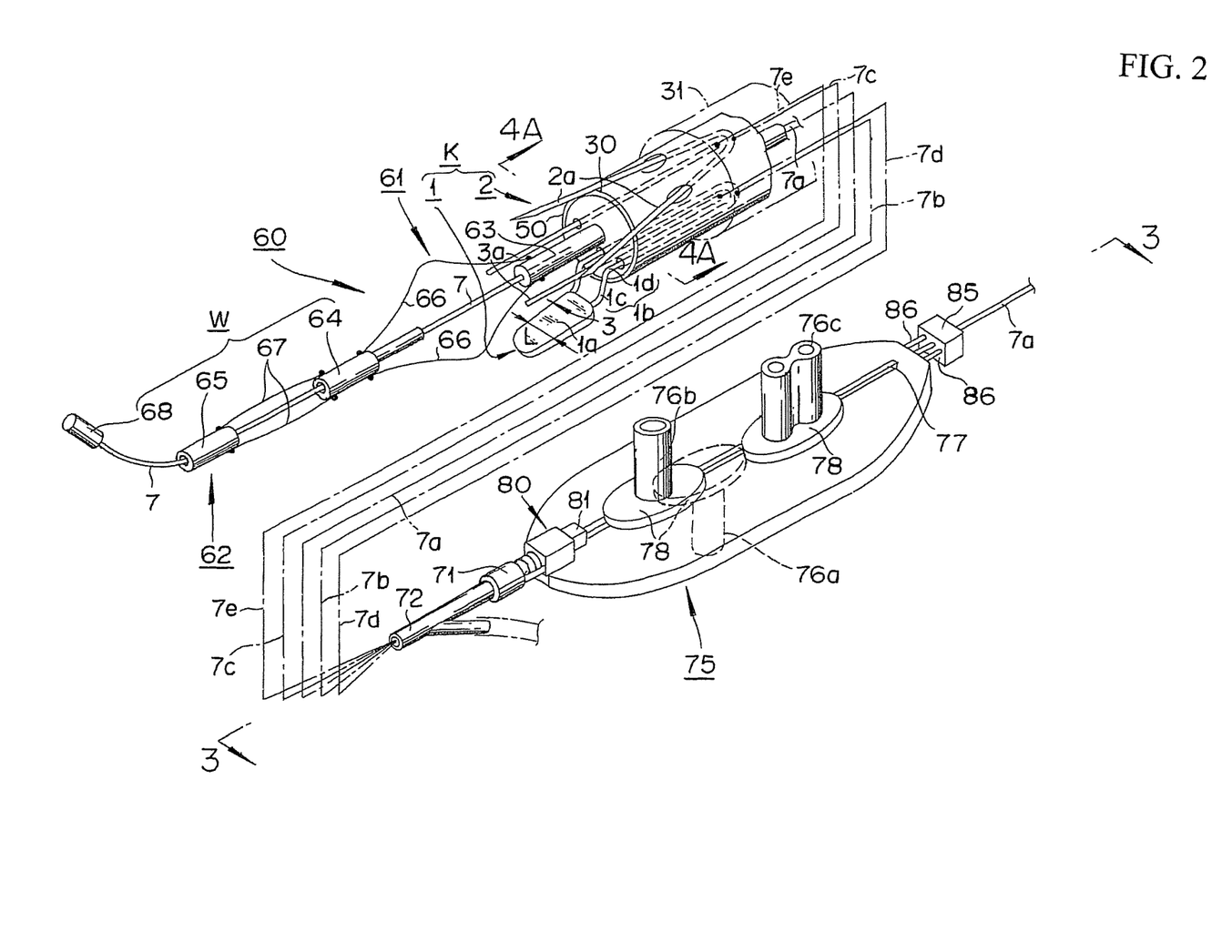
FIG. 2 is a perspective view of a main portion showing one example of the PFO closing device.

This device, as shown in FIGS. 1 and 2, includes an operation unit (hand operated unit) 70 provided on the proximal side or nearer to the user's (doctor's) hands; a guiding catheter 31 mounted on the operation unit 70 for the proximal tip thereof; a catheter 30 provided in the guiding catheter 31, a clamper K provided at a distal portion of the catheter 30; and a positioning hold mechanism 60 for executing the procedure relatively stably and accurately by the clamper K. It should be noted in the following explanation that the side of the operation unit of the device is referred to as the proximal side and the side of the clamper K or the foramen ovale valve M2 is referred to as the distal side.

The clamper K of the present exemplified embodiment is comprised, as shown in FIG. 2, of a sandwich member 1 directly contacting one side surface of the atrial septum secundum M1 and a stick portion (needle portion) 2 which is stuck into the foramen ovale valve M2. The sandwich member 1 and the stick portion 2 whose proximal portions are held by a holder 50 provided at the distal tip of the catheter 30 are configured so as to take positions facing (opposing) each other when they protrude from the holder 50.

The sandwich member 1 is constituted by a main body portion 1a possessing a flat plate shape and a predetermined width L and a pair of wire portions 1b connected to the proximal portion of the main body portion 1a. One part of an operation member 7b is connected to the proximal side of the wire portion 1b. By moving the operation member 7b forward and backward in the axial direction, the sandwich member is displaced so as to protrude from the distal tip of the catheter 30 or so as to approach toward the stick portion 2 side.

Figure 4A:
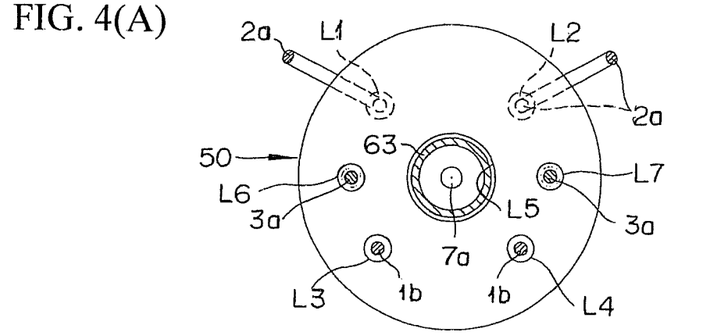
FIG. 4A is a cross-sectional view taken along the section line 4A-4A in FIG. 2.

The wire portion 1b includes a bend portion 1c and a straight-shaped portion 1d. The straight-shaped portion 1d is positioned in lumens L3, L4 (see FIG. 4) of the holder 50 so as to be movable forward and backward, so that if the operation member 7a is operated, it is possible, when the bend portion 1c enters into the entrance portion of the lumens L3, L4 of the holder 50, to displace the sandwich member 1 so it approaches or moves away from the stick portion 2 and it is possible to sandwich the biological tissue relatively easily and smoothly even in case of the distal portion of the fine catheter 30.

With respect to the sandwich member 1, a material which does not exert bad influence to a living body is used for a material of the main body portion 1a. The sandwich member is preferably a non-electrically-conductive member. Examples of preferred materials for fabricating the sandwich member include, for example, polyimide resin, polyurethane, PET, nylon, fluorine resin, polypropylene and the like. Alternatively, it is also possible to use a member in which the surface of a metallic material is coated with an electrical insulation film.

The stick portion 2 is positioned in or held by lumens L1, L2 formed in the holder 50 so as to be movable forward and backward. The distal portion of the stick portion 2 is constructed so as to be retractable from the holder 50 by operating an operation member 7c connected to the proximal side. More specifically, the stick portion 2 and the sandwich member 1 of the clamper K are both movable independently in the axial direction with respect to the catheter 30, but the stick portion 2, differently from the sandwich member 1, is retractable from the holder 50 and can be made to protrude freely at a desired position.

By making each of the stick portion 2 and the sandwich member 1 of the clamper K movable independently with respect to the catheter 30 by using the operation members 7b, 7c in this manner, it is possible to stick the stick portion 2 at an arbitrary position, so that it is possible to execute the procedure quite smoothly, safely and also certainly.

In particular, the stick portion 2 of the present exemplified embodiment is comprised of two pieces of needle members 2a, 2a and is constructed such that both the needle members 2a, 2a move in/out from the distal region of the catheter 30 in a tilting manner with respect to the axis of the catheter 30 and in other words, such that they move in/out from the side direction of the catheter 30. Therefore, for example, to explain it with reference to FIG. 6, it is ideal for the sticking position which is to be stuck to be a foramen ovale valve portion in close vicinity of the position at which the foramen ovale valve M2 and the atrial septum secundum M1 overlap (T portion shown by alternate long dashed short dashed line), so that if such a sticking position is approached, it becomes possible to execute the sticking by aiming at this portion.

The cautery device 3 of the present exemplified embodiment includes two pieces forming electrodes or electrode portions 3a, 3a which function as a positive pole and a negative pole respectively. The electrode portions 3a, 3a are positioned in and held by lumens L6, L7 formed in the holder 50 so as to be movable forward and backward. The distal portions of the electrode portions are constituted so as to be retractable from the holder 50 by operating operation members 7d, 7e connected to the proximal sides. In other words, the electrode portions 3a, 3a are constituted to be movable independently in the axial line direction with respect to the catheter 30, and it happens that they can be protruded freely at a desired position. Therefore, it is possible to execute the procedure quite smoothly, safely and also certainly.

The material forming the electrode portions 3a, 3a may be a SUS material, but it is preferable to use a material which does not exert bad influence to a living body such as, for example, gold, silver, platinum, tungsten, palladium or alloys of these, Ni—Ti alloy, titanium alloy and the like.

It is preferable, although not particularly limited, for the mutual distance of the two electrode portions 3a, 3a to be selected such they can be inserted into the foramen ovale O while also occupying the width of the foramen ovale O in a certain amount of region. More specifically, two pieces forming the electrode portions 3a, 3a are inserted into the foramen ovale O and thereafter, in a state in which the tissues of the atrial septum secundum M1 and the foramen ovale valve M2 are sandwiched by the clamper K and the foramen ovale O is closed, electric energy is supplied to the electrode portions 3a, 3a. At that time, energization between the electrode portions 3a, 3a is executed (bipolar system). In particular, if it is formed as a bipolar system for controlling the current by the impedance of the biological tissue between the electrode portions 3a, 3a, there are advantages in that a correspondence exists in with respect to the state of the tissues of the foramen ovale valve M2 and the atrial septum secundum M1 which differ depending on a person, and the safety and the convenience of the procedure are obtained. More specifically, based on a fact that the fusion of the biological tissue M between the two pieces of the electrode portions 3a, 3a occurs relatively easily, it is satisfactory if the distance of the two pieces of electrode portions 3a, 3a is set so as to occupy the width of the foramen ovale O over a certain amount or region. It should be noted that the two pieces forming the electrode portions 3a, 3a of the present exemplified embodiment are positioned approximately in parallel, but it is possible, for example, to provide them in a shape expanded in a way of widening toward the distal side (e.g., the electrode portions 3a, 3a can be configured to diverge away from one another toward the distal direction) or to provide them in a tapered shape, and it is satisfactory if it can be changed accordingly corresponding to the shapes of the foramen ovale O. In order to change the shape of the electrode portions 3a, 3a, they can be elastically-deformed by moving them so they protrude distally outward from a state in which the electrodes are housed in the lumens L6, L7. If the electrode portions 3a, 3a are configured to possess a shape expanding in a widening (diverging) manner in the distal direction, the electrode portions will naturally expand or move away from one another as the electrode portions 3a, 3a are moved forward. Alternatively, it is also possible for the electrode portion 3a, 3a to protrude along the direction of the lumens L6, L7 by changing the direction with which the lumens L6, L7 are formed in the catheter 30. That is, the divergence or widening of the electrode portions 3a, 3a can be achieved by appropriately configuring the lumens L6, L7 that receive the electrodes portions 3a, 3a so that the lumens guide the electrode portions 3a, 3a in a widening or diverging manner in the distal direction.

Also, with respect to the number of electrode portions 3a, it may be not only two pieces but also one piece or a larger number of pieces than two. In a case in which the electrode portion 3a is formed by three or more pieces, respective electrode portions 3a will function as either one of a positive pole and a negative pole. It should be noted that the electrode portion 3a can be formed by one piece and also all the plurality of electrode portions 3a can be formed by active electrodes (monopolar system). In this case, a pole forming a counterpart (or return electrode) for the electrode will be provided, for example at the stick portion 2, at the sandwich member 1 or on the outside of the body. In a case in which a pole forming a counterpart is provided at the stick portion 2 or at the sandwich member 1, the stick portion 2 or the sandwich member 1 is formed by an electrically-conductive member and the operation member 7b or 7c coupled to the stick portion 2 or the sandwich member 1 is formed by an electrically-conductive member, thus there is connected the energy supply unit 20 through the operation member 7b or 7c from the proximal side of the catheter 30.

The present device includes a positioning hold mechanism 60 (described in detail later) provided with a main tube 63 positioned in a large lumen L5 at the center of the holder 50 and a main operation rod 7a. Before using the sandwich mechanism K, the stick portion 2 is positioning-held by using the positioning hold mechanism 60 and in this case, the sticking is executed in a state in which the main operation rod 7a is inserted into the foramen ovale O beforehand. In other words, the stick portion 2 is configured so as to stick into (penetrate) the foramen ovale valve portion by passing through a passway which is restricted a certain degree by the main operation rod 7a.

If the stick portion 2 is operated in such a state, there is a fear that the sticking can be carried out only for the front side of catheter 30. However, if the needle members 2a, 2a can be protruded to the side direction similarly as the present exemplified embodiment, it is naturally directed toward a closed position of the ideal overlapping position T as the distal tip of the catheter 30 approaches the foramen ovale O. Moreover, it is possible for the stick portion 2 to execute the sticking action independently, so that the most preferable sticking position is to be chosen and the sticking becomes possible at that position.

Figure 4B:
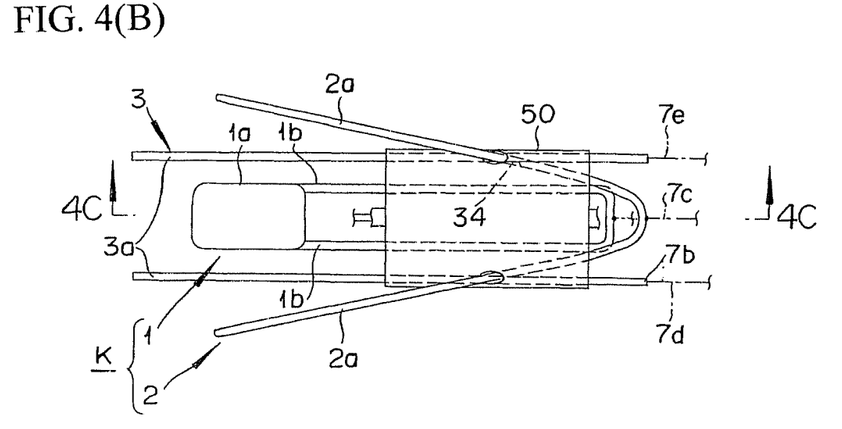
FIG. 4B is a plan view of the portion of the closing device shown in FIG. 4A.
Figure 4C:
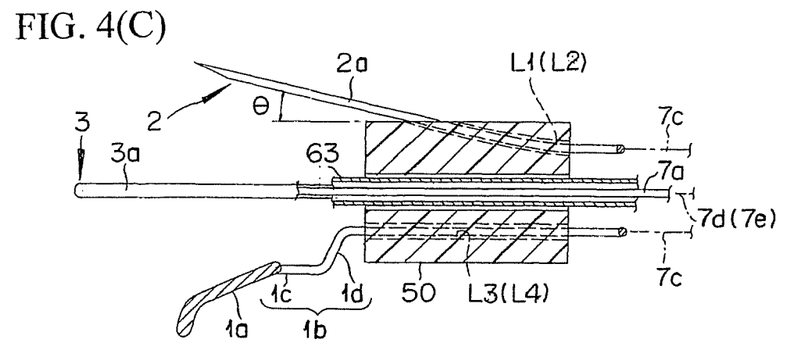
FIG. 4C is a cross-sectional view taken along the section line 4C-4C in FIG. 4B.

As a mechanism for retracting the stick portion (needle members 2a, 2a) in the side direction, as shown in FIG. 4A to FIG. 4C, two lumens L1, L2 are formed in the holder 50 for the stick portion 2. The lumens are formed so as to tilt or be inclined toward the side surface of the distal region from the proximal side end surface (the lumens diverge outwardly away from the central axis of the holder member in the direction toward the distal end of the holder 50), and both the needle members 2a, 2a are guided by the lumens L1, L2 so as to protrude in the side direction of the catheter 30. It is possible for the tilt angle θ of this tilt portion 34 to be set to any value, but generally, around 10° to 30° is preferable and according to circumstances, it is also possible to set it around 90°. The tilt portion 34 is tilted or angled so as to diverge away from the sandwich member 1, but it is not limited only by this construction. For example, it is also possible, as shown in FIG. 4B, to form both the needle members 2a, 2a so as to diverge away from one another in a widening manner in the distal direction. If the stick portion is formed in a widening manner, the foramen ovale valve M2 is stuck in a wider region and the sandwich region with respect to the sandwich member is widened.

Also, according to circumstances, although it is not shown in the drawing, it is also possible for both the needle members 2a, 2a themselves to be curved in arc shapes in the direction away from the sandwich member 1 or to be bent in "<" shapes. If needle members are used which have a curved or bent needle shape, it becomes relatively easy to further protrude the needle members 2a, 2a to the side direction by simply moving the needle members 2a, 2a in the axial direction of the catheter 30.

The stick portion 2 of the present exemplified embodiment is comprised, as shown in FIG. 2, of two fine pieces or the needle members 2a, 2a whose cross-sections perpendicular to the axes are circles and whose front ends are sharply pointed. The two pieces are mutually separated and if the foramen ovale valve M2 is stuck into by such a stick portion 2, it is possible, even for various forms of the foramen ovale valve and the atrial septum secundum, to execute positioning of at least one needle member 2a to the foramen ovale valve M2 and the sandwich operation of the biological tissue M becomes relatively easy.

It is not always necessary for the needle members 2a, 2a to be solid cylindrical members as it is possible to employ hollow cylindrical shaped members and it is preferable for the outer diameter thereof to be around 0.1 mm to 2 mm in order to be installed in the catheter 30. For the material forming the needle members 2a, 2a, a material which does not exert bad influence to a living body is used, but it is preferable to employ a non-electrically-conductive member and it is preferable to use, for example, polyimide resin, polyurethane, PET, nylon, fluorine resin, polypropylene and the like. Alternatively, it is also possible to use a member in which the surface of a metallic material is coated by an electrical insulation film. Alternatively, it is also possible to use a metallic material if it is insulated from the energy supply unit 20. Although not particularly limited, it is sufficient if the mutual distance of the two pieces of the electrode portions 3a, 3a is selected such that the foramen ovale valve M2 and the atrial septum secundum M1 can be sandwiched in a certain range. Also, with respect to the number of pieces forming the electrode portions 3a, 3a, it may be not only be comprised of two pieces but also a larger number of pieces than two.

As the operation members 7b, 7c, 7d, 7e for moving the sandwich member 1, the stick portion 2 and the electrode portions 3a, 3a in/out from the catheter 30, any kind of members can be employed if they are fine wire-shaped members and can move the clamper K forward and backward in the catheter 30. It is preferable to use a wire such as, for example, stainless steel, Ni—Ti, titanium and the like. The operation members 7b, 7c are inserted into the catheter 30 and are connected with operation levers 76a, 76b described later. The operation members 7d, 7e are positioned in the catheter 30 and are connected with the energy supply unit 20 through an operation lever 76c, connection members 21a, 21b, conductive wires d1, d2 and a control unit 22 which will be described later.

It should be noted that the holder 50 includes, as shown in FIG. 4A, a plurality of lumens L1 to L7, but it is also possible for these respective lumens L1 to L7 to be constituted by catheters respectively.

Figure 3:
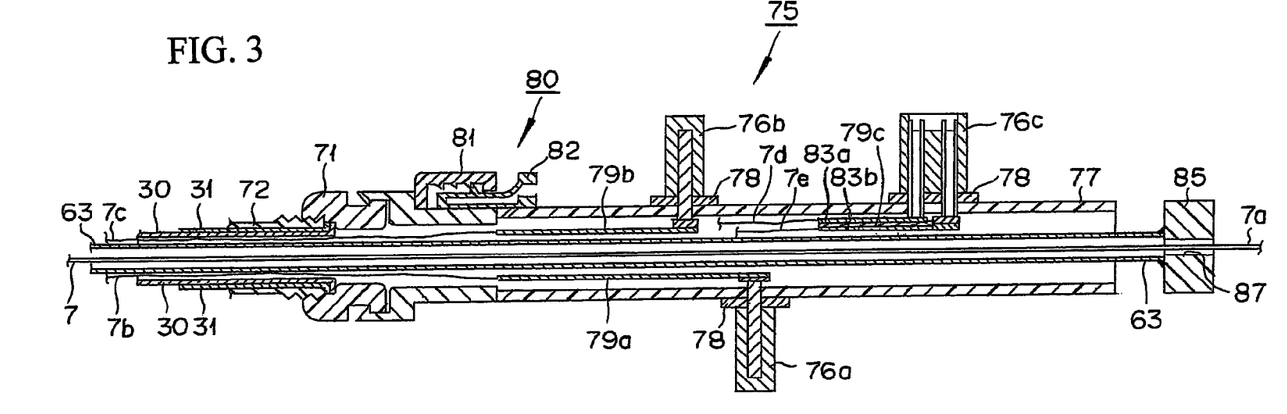
FIG. 3 is a cross-section view taken along the section line 3-3 in FIG. 2.

As shown in FIG. 1 to FIG. 3, the operation unit 70 includes a handle member 75 composed of a flat member such that the surgery operator can grasp it by a single hand. Protruding or extending from the side surface (upper side surface) of the handle member 75 are the operation lever 76b coupled with the proximal side of the operation member 7c of the stick portion 2 and the operation lever 76c coupled with the proximal side of the operation members 7d, 7e of the electrode portions 3a, 3a. Protruding or extending from the rear side surface (lower side surface) of the handle member 75 are the operation lever 76a for operating the operation member 7b of the sandwich member 1.

The operation lever 76c is provided slidably in a slide groove 77 formed on the handle member 75 and a brim portion 78 is provided at the lower end portion, in which it is configured to be able to slidingly move smoothly without falling out of the handle member 75.

The operation members 7d, 7e are wired to the operation lever 76c (e.g., the end portion of the operation lever 76c). In addition, two connection members 21a, 21b composed of sockets, couplers or the like are provided at the distal tips of the conductive wires d1, d2 which extend from and are electrically connected to the electric energy supply unit 20. The connection members 21a, 21b are adapted to concave-convex-fit in a detachable manner with the upper end portions of the operation lever 76c. When the connection members 21a, 21b are fitted to the operation lever 76c, the electric energy supply unit 20 and the operation lever 76c are in an electrically conductive state so that energization between the electrode portions 3a, 3a can be executed. Disconnecting the connection members 21a, 21b from the operation lever 76c ceases energization between the electrode portions 3a, 3a.

Consequently, after the procedure involving the sticking and the sandwiching produced by operation of the operation levers 76a, 76b is completed, if the connection members 21a, 21b are connected to the operation lever 76c, it is possible to supply electric energy by which the foramen ovale valve M2 and the atrial septum secundum M1 are fused. In other words, not only is it possible to supply electric energy at a desired point in time but also it is possible to execute the procedure accurately and also smoothly in case of executing the procedure without concern that the conductive wires d1, d2 will become obstructive.

It is possible to directly connect the respective operation members 7b, 7c with the respective operation levers 76a, 76b by brazing or the like, but in the present exemplified embodiment, there are provided slide pieces 79a, 79b that face the slide groove 77 formed on the handle member 75, the proximal sides of the respective operation members 7b, 7c are brazed on the distal tips of the slide pieces 79a, 79b and the inner ends of the respective operation levers 76a, 76b are brazed on the proximal tips of the slide pieces 79a, 79b. With this construction, not only is the operability of the device improved but also the strength or the durability is improved and it is preferable. It should be noted that the slide pieces 79a, 79b are provided slidably in the groove formed on the handle member 75.

In addition, it is possible also for the respective operation members 7d, 7e to be directly connect with both the electrodes of the operation lever 76c by brazing or the like, but in the present exemplified embodiment, there is provided a slide piece 79c facing the slide groove 77 formed on the handle member 75 on the slide piece 79c, there are arranged two electrically-conductive portions 83a, 83b contacted individually with the electrodes of the operation lever 76c. In addition, the proximal sides of the respective operation members 7d, 7e are brazed at the respective electrically-conductive portions 83a, 83b of the distal side of the slide piece 79c, and the inner ends of the respective electrodes of the operation lever 76c are brazed at the respective electrically-conductive portions 83a, 83b of the proximal tip of the slide piece 79c. With this construction, not only is the operability of the device improved but also the strength or the durability is improved and it is preferable. It should be noted that the slide piece 79c is provided slidably in the groove formed on the handle member 75.

In addition, the operation unit 70 of the present exemplified embodiment also includes a lock mechanism 80 for locking a state in which the stick portion 2 protrudes from the distal portion of the catheter 30 at the distal portion of the handle member 75.

The lock mechanism 80 is constructed to include a bump member for restricting the sliding movement of the operation lever 76b for the needle on the distal side of the slide groove 77 formed on the handle member 75, and the sliding movement is locked by pressing the operation lever 76b for the needle to the bump member. If the stick portion 2 is locked in a state of protruding from the distal portion of the catheter 30, it is possible to supply electric energy while maintaining the protruding state of the stick portion 2, the stick portion 2 does not deviate or move at the time of supplying electric energy and it is possible to carry out the procedure more stably and also accurately.

It is also possible for the lock mechanism 80 to be differently constructed so long as it is possible to lock the operation lever 76b for the needle. As shown in FIG. 3, if a tubular block 81 is fixed on the handle member 75 and a slide member 82 is provided movably in the tubular block 81, it is possible to adjust the fixed position of the operation lever 76b for the needles (stick portion 2) and it is preferable.

Also, in order to lock the operation lever 76c for the electrode portion, it is also possible to provide a lock mechanism of the same structure.

The energy supply unit 20 is a unit for supplying electric energy to the cautery device 3 and a well-known system is employed, so that a detailed description is not set forth. If easiness of control is taken into account, it is preferable to employ an electrical power supply regardless of whether it is a direct-current power supply or an alternate-current power supply. However, it is also possible to employ not only this kind but also any kind of supply unit if it can supply energy for permitting the foramen ovale valve M2 and the atrial septum secundum M1 to be melted by the heat and pressed and fixed by an adhesive agent such as collagen, erastin and the like. For example, it is also possible to use a super sonic wave, laser, microwave or high frequency and the like.

Seven lumens L1 to L7 are established in the holder 50 as shown in FIG. 4, and the stick portion 2 and the sandwich member 1 are positioned in the first and second lumens L1, L2 and the third and fourth lumens L3, L4 as mentioned above. The electrode portions 3a, 3a are positioned in the fifth and the sixth lumens L6, L7, and the positioning hold mechanism 60 is provided in the fifth lumen L5 having the maximum aperture which exists at the center.

The positioning hold mechanism 60, as shown in FIG. 2, generally, includes a positioning portion 61 for positioning the stick portion 2 with respect to a foramen ovale O and a holding portion 62 for holding the foramen ovale valve M2 with respect to the sticking direction of the stick portion 2 so as not to allow the backward movement thereof, and normally it is housed in the guiding catheter 31, but it is pushed out from the guiding catheter 31 by the main operation rod 7a and the main tube 63 when using it.

To describe it in more detail, a main tube 63 is positioned in the center lumen L5 for pulling and withdrawing the positioning hold mechanism 60 in/from the catheter and for purpose of reinforcement of the catheter 30; and a main operation rod 7a which is provided so as to move forward and backward freely in the axial direction in the main tube 63.

There is provided at the distal portion of the main tube 63 the positioning hold mechanism 60 including a positioning portion 61 and a hold portion 62. The positioning portion 61 is operated to radially outwardly expand or shrink by the operation of the main operation rod 7a and is comprised of a pair of first elastic wires 66 coupling the main tube 63 and a middle sleeve body 64; and a hold portion 62 comprised of a bump or contact member 68 provided at the distal portion of the main operation rod 7a, a distal tip sleeve body 65 and a pair of a second elastic wires 67 coupling the middle sleeve body 64 and the distal tip sleeve body 65, and which holds the foramen ovale valve M2 by the contact member 68 and the distal tip sleeve body 65.

With respect to the positioning portion 61, the main operation rod 7a protrudes from the distal tip of the main tube 63, the first elastic members 66 are displaced inward and outward by the operation of moving the main operation rod 7a forward and backward in the axial direction, respective first elastic members 66 press an inner fringe of the foramen ovale O with approximately equal elastic forces, and the stick portion 2 and the cautery device 3 are center-aligned with respect to the foramen ovale O. In other words, the positioning portion 61 exhibits a function for positioning the stick portion 2 and the cautery device 3 which are positioned between both the first elastic members at the center portion of the foramen ovale O.

The holding portion 62 includes a bending mechanism W for bending the distal portion of the main operation rod 7a by operating the main operation rod 7a in the axial direction so as to move forward and backward. The bending mechanism W bends the holding portion 62 so as to face the direction in which the stick portion 2 sticks the foramen ovale valve M2 and exhibits a function for holding the foramen ovale valve M2. In other words, the bending mechanism W operates to bend the holding portion 62 to bend back upon itself. Here, the bending mechanism W is constituted by the middle sleeve body 64, the distal tip sleeve body 65, the second elastic wire 67 for coupling both the sleeve bodies 64, 65, and the contact member 68.

The proximal tip of the first elastic wire 66 is welded on the distal tip of the main tube 63 and the distal side thereof is welded on the middle sleeve body 64. On the other hand, the proximal tip of the second elastic wire 67 is welded on the distal tip of the middle sleeve body 64 and the distal side thereof is welded on the distal tip sleeve body 65.

It is preferable for a specific example of the first and second elastic wires 66, 67 to use a metallic wire such as stainless steel, nickel-titanium, super elastic alloy (for example, Ni—Ti alloy) and the like with an outer diameter of around 0.1 mm to 0.5 mm. It is also possible to prevent the tissue from being wounded by coating a metallic wire with a (soft) resin tube.

The holding portion 62 is constructed such that the first elastic wire 66 of the proximal side bends prior to the second elastic wire 67 of the distal side; the positioning of the stick portion 2 is executed; subsequently, the main operation rod 7a itself is deformed accompanied by the contact member 68 and the distal tip sleeve body 65; and the positioning portion 61 holds the foramen ovale valve M2 after positioning the stick portion 2.

For such a construction, for example, it is also possible to use a second elastic wire 67 having higher material stiffness than that of the first elastic wire 66. Also, an easily-deformable portion can be formed by, for example, bending a portion of the first elastic wire 66 beforehand, and when a traction force or backward force is applied, the first elastic wire 66 is bent first compared with the second elastic wire 67 by the deformation of the easily-deformable portion.

When constructed in this manner, the first elastic wire 66 of the proximal side engages an inner fringe of the foramen ovale O simply by the movement of the main operation rod 7a backward and so the positioning of the stick portion 2 can be executed. When applying further movement, the second elastic wire 67 of the distal side is protrudes and deforms like an arc shape toward the outward direction in the radial direction and it is possible to hold the foramen ovale valve M2 so as not to allow the backward movement thereof such that it becomes relatively easy to stick the stick portion 2 into the foramen ovale valve M2.

Also, the main operation rod 7a is configured to be 360° rotatable centering around the axial line in the main tube 36 (i.e., the axis of the main tube 36). With the main operation rod 7a being 360° rotatable, when the distal tip of the main operation rod 7a is inserted up to the vicinity of the foramen ovale O, it is possible to position-change the main operation rod 7a rotatingly and even if a state of the foramen ovale O is deformed variously, it is possible, regardless of the shape state thereof, to insert the distal tip of the device into the foramen ovale O and it is possible not only to simplify the procedure but also to execute it speedily.

There is provided at the rear end portion of the handle member 75 a handle member for main tube 85 which moves the main tube 63 forward and backward through two pieces of slide rails 86. The proximal side of the main tube 63 is firmly fixed at the handle member for main tube 85, so that when the handle member for main tube 85 is pulled away from the handle member 75, in other words, when it is pulled backward, it is possible to pull the main tube 63 into the center lumen L5 of the catheter 30 and according to this, it is possible to withdraw the whole positioning hold mechanism 60 into the catheter 30.

It should be noted that in order to configure the main operation rod 7a to be 360° rotatable, the main operation rod 7a is inserted into a through-hole 87 of the handle member for main tube 85 and is extended.

For the material constituting this main tube 63, it is possible to use a deformable elastic material such as, for example, polyimide resin, polyurethane, PET, nylon, fluorine resin, polypropylene and the like.

Also, it is also possible for the main operation rod 7a to employ any kind of rod if it is a fine hollow cylindrical wire and possesses a comparison suitability, but it is preferable to use a fine tube such as, for example, stainless, Ni—Ti, titanium and the like.

A Y connector 72 into which a contrast medium or the like can be injected is coupled to the distal tip of the handle member 75 through a coupling member 71, and the proximal tip of the catheter 30 and the end portion of the guiding catheter 31 are held at the coupling member 71.

With respect to the guiding catheter 31 of the present exemplified embodiment, the distal tip thereof is bent gently in an arc shape in order to make it easier to insert into the foramen ovale O between the foramen ovale valve M2 and the atrial septum secundum M1. The foramen ovale valve M2 and the atrial septum secundum M1 differ depending on the person, so that when the distal tip of the guiding catheter 31 is bent, the guiding catheter 31 itself is rotatingly moved and it is possible to insert the guiding catheter 31 into the foramen ovale O at a position in which the insertion becomes easiest, and safety and convenience of the procedure are improved compared with the case of a straight shape.

Next, the operation of the present exemplified embodiment will be explained.

It should be noted in FIG. 8A to FIG. 8D that the shapes and positions of the second elastic wire 66 are drawn approximately flush with the sandwich member 1 and the stick portion 2, but in order to facilitate the understanding, they are shown in positions displaced by 90° and those are different from the actual deformation states.

First, the surgery operator moves the handle member for main tube 85 of the operation unit 70 backward with respect to the handle member 75 and makes a state in which the sandwich member 1, the stick portion 2, the electrode portions 3a, 3a and the like are housed in the guiding catheter 31. In this state, the distal tip of the guiding catheter 31 is inserted from a predetermined position of the living body by using a guide wire as a guide and until it reaches the right atrium R by passing through the femoral vena cave J. Here, it is also possible to insert only the guiding catheter 31 into the living body and afterward to insert the catheter 30 by using that guiding catheter 31 as a guide.

Figure 5:
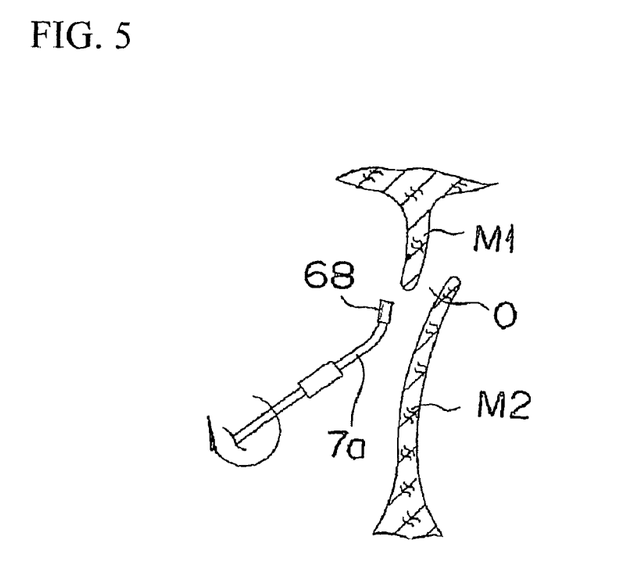
FIG. 5 is a cross-sectional schematic view showing a main operation rod and a cautery device inserted into a foramen ovale.

When the distal tip of the guiding catheter 31 reaches the right atrium R, as shown in FIG. 5, the catheter 30 is pushed out and moved toward the foramen ovale O between the foramen ovale valve M2 and the atrial septum secundum M1. The distal tip of the guiding catheter 31 is curved, so that it is possible to move it toward the foramen ovale O comparatively easily.

Figure 8A:
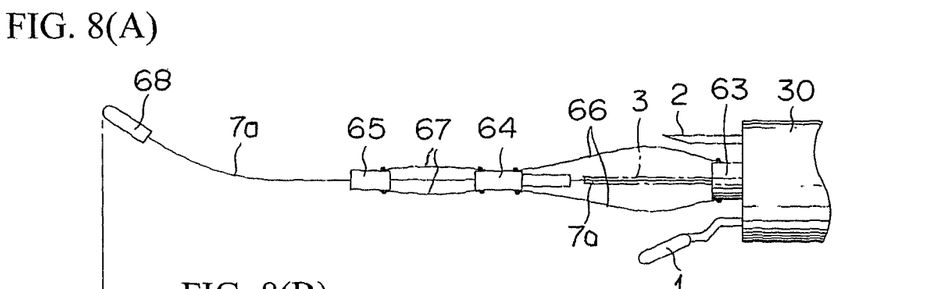
FIG. 8A to FIG. 8D are plan views showing operation states of the PFO closing device.

Next, the main operation rod 7a is moved forward and, as shown in FIG. 8A, the distal tip of the main operation rod 7a protrudes from the distal tip sleeve body 65 and is inserted into the left atrium L. It is possible to visually observe this protruding state from the outside if a marker is provided on the contact member 68 or the like, and it is possible to identify the position of the distal tip of the main operation rod 7a by touch when the distal tip of the main operation rod 7a contacts an inner wall of the left atrium L or the like according to this protrusion even in a case in which it is difficult to visually observe. In the present exemplified embodiment, the main operation rod 7a is made to be rotatable by 360°, so that, as shown in FIG. 5, when the main operation rod 7a is moved forward while rotating, it is possible to insert it into the foramen ovale O relatively easily.

Figure 8B:
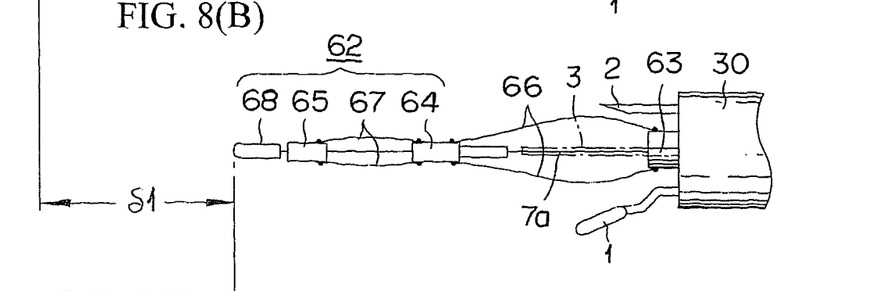

After the identification of the distal position of the main operation rod 7a, as shown in FIG. 8B, the main operation rod 7a is moved backward until the contact member 68 of the main operation rod 7a contacts the distal tip sleeve body 65 (amount of backward movement is 51 in FIG. 8B). Then, the handle member 75 is operated, and the second elastic wire 67, the sandwich member 1, the stick portion 2 and the cautery device 3 are positioned in the vicinity of the foramen ovale valve M2 and the whole holding portion 62 is inserted into the left atrium L side.

Next, the handle member 75 is operated and the electrode portions 3a, 3a are protruded (extended) and inserted into the foramen ovale O.

Figure 8C:
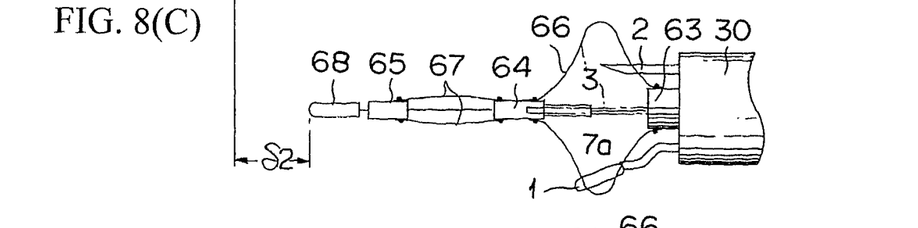

Thereafter, when the main operation rod 7a is further moved backward (amount of backward movement is 52 in FIG. 8C), the operation force for the backward movement is transmitted by the main operation rod 7a to the first elastic wire 66 firmly fixed on the distal tip of the main tube 63 through the contact member 68, the distal tip sleeve body 65, the second elastic wire 67 and the middle sleeve body 64, and the first elastic wire 66 is, as shown in FIG. 8C, protruded and deformed in an arc shape toward the outside direction in the radial direction. However, at this time point, the second elastic wire 67 is not deformed.

Consequently, the first elastic wire 66 is deformed (radially outwardly expanded) while pushing and widening the opening edge portion of the foramen ovale O, so that the stick portion 2 and the cautery device 3 which are provided in close vicinity of the first elastic wire 66 is center-aligned with respect to the foramen ovale O, and the stick portion 2 and the cautery device 3 are positioned at the center of the foramen ovale O.

Figure 6:
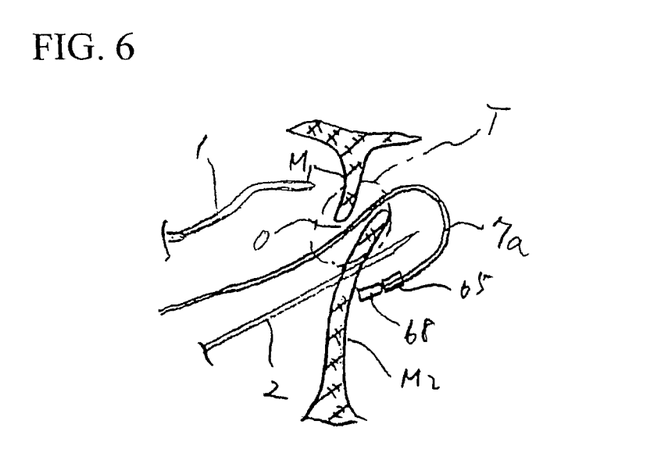
FIG. 6 is a cross-sectional schematic view of a state in which a foramen ovale valve is held and a needle portion is stuck thereto.
Figure 8D:
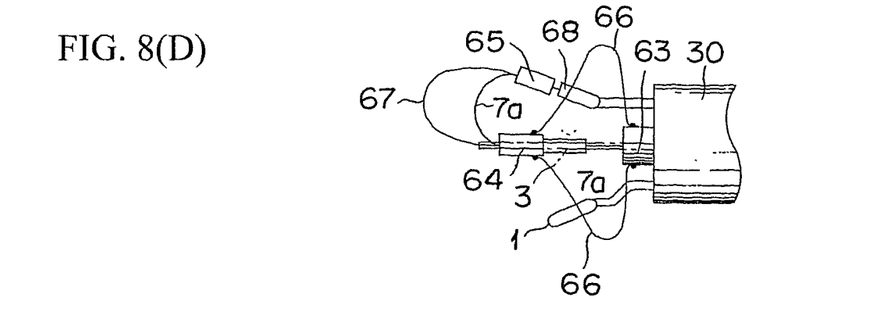

Further, when the main operation rod 7a is operated to move backward until the rear end of the middle sleeve body 64 is attached to the distal tip of the main tube 63, as shown in FIG. 8D, the first elastic wire 66 is not deformed so much, but the second elastic wire 67 of the distal side is protruded and deformed in an arc shape toward the outside direction in the radial direction by the operation force. Consequently, as shown in FIG. 6, in the left atrium L, the contact member 68 and the distal tip sleeve body 65 approach the stick portion 2, so that the contact member 68 and the distal tip sleeve body 65 contact the surface of the left atrium side of the foramen ovale valve M2 and hold this.

In this state, the operation lever 76b for the needle is moved forward until it contacts or engages the lock mechanism 80, and the stick portion 2 protrudes from the side portion of the catheter 30 through the operation member 7c. When the operation lever 76b for the needle is moved forward, it is possible to execute the sticking (i.e., the sticking portion or needle portion 2 being stuck into the foramen ovale valve) at an ideal position in the vicinity of the overlapping position of the atrial septum secundum M1 and the foramen ovale valve M2. On an occasion of this sticking, as shown in FIG. 6, the atrial septum secundum M1 and the foramen ovale valve M2 exist between the sandwich member 1 and the stick portion 2. At the same time, the electrode portions 3a, 3a are sandwiched between the atrial septum secundum M1 and the foramen ovale valve M2.

Also, when the stick portion 2 is stuck once, the position of the stick portion 2 becomes position-fixed, that is, is made to be positioned in relation to the foramen ovale valve M2, so that in this step, the main operation rod 7a is returned once and, as shown in FIG. 8B, the first elastic wire 66 and the second elastic wire 67 are changed over to be in a straight-line shape and thereafter, the handle member 85 for the main tube is operated so as to move backward. The main tube 63 is thus moved backward, and the whole positioning hold mechanism 60 is withdrawn in the lumen L5 of the catheter 30.

Figure 7:
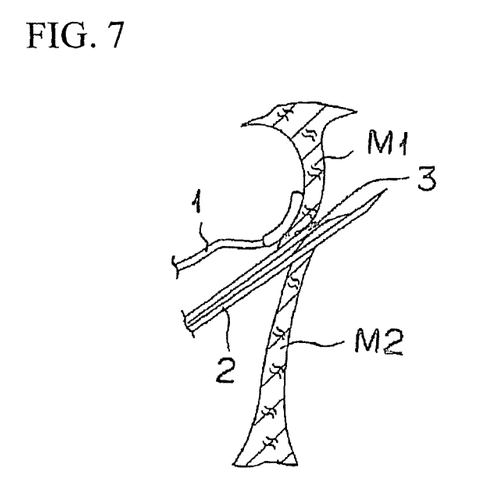
FIG. 7 is a cross-sectional schematic view in which a foramen ovale valve and an atrial septum secundum are sandwiched by a needle portion and a sandwich member.

After this withdrawal, when the operation lever 76a for the sandwich member is operated to move backward and the sandwich member 1 is moved backward through the operation member 7b, the bend portion 1c of the sandwich member 1 interacts with the lumen in the end portion of the holder 50 so that the sandwich member approaches the stick portion 2 side. As shown in FIG. 7, the atrial septum secundum M1 and the foramen ovale valve M2 are firmly sandwiched between the sandwich member 1 and the stick portion 2. It should be noted that the sandwich member 1, the positioning hold mechanism 60 and the stick portion 2 can respectively move independently, so that the device may not always be operated by such a sequence mentioned above. For example, it is also possible to stick the foramen ovale valve M2 with the stick portion 2 after a state in which the sandwich member 1 is moved and the atrial septum secundum M1 is held by the sandwich member 1 and thereafter operate the positioning hold mechanism 60 so that the atrial septum secundum M1 and the foramen ovale valve M2 are sandwiched and held between the electrode portions 3a, 3a.

If the operation lever 76b for the needle is pressed to the lock mechanism 80 and a lock state is maintained, a sandwich state of the atrial septum secundum M1 and the foramen ovale valve M2 caused by the sandwich member 1 and the stick portion 2 is maintained. By this lock, there is little concern that the stick portion 2 is deviated or moved, so that if the connection members 21a, 21b are concave-convex-fitted to the operation lever 76c for the electrode portion, a predetermined electric current controlled by the control unit 22 flows from the operation lever 76c for the needle into the electrode portions 3a, 3a through the operation members 7d, 7e. The atrial septum secundum M1 and the foramen ovale valve M2 are heated by the supply of this electric energy. At that time, the electrode portions 3a, 3a are positioned on the fusion surface between the atrial septum secundum M1 and the foramen ovale valve M2, so that it is possible to input electric energy efficiently and it is possible to execute the fusion while keeping damage to the biological tissue M to a minimum. Also, the electrode portions 3a, 3a are positioned on the fusion surface, so that the fusion force does not depend on the thickness of the atrial septum secundum M1 and the foramen ovale valve M2 which are sandwiched by the clamper K and it is possible to repress fluctuation of the fusion force as small as possible.

By controlling electric energy in the control unit 22, even if a portion of the electrode portions 3a, 3a is exposed in the blood, it is possible in this step to prevent the thrombus from being attached to the electrode portions 3a, 3a. However, if coating for preventing thrombus attachment is applied on the surfaces of the electrode portions 3a, 3a, it happens that the attachment of the thrombus is prevented more certainly and it is preferable.

When the heating is continued while maintaining a fusion temperature, the tissues of the atrial septum secundum M1 and the foramen ovale valve M2 melt and are fused mutually by an adhesive agent such as collagen, erastin and the like.

When the fusion is completed, the energization is stopped, the operation lever 76b for the needle, the operation lever 76a for the sandwich member and the operation lever 76c for the electrode portion are moved backward and are housed in the guiding catheter 31. Then, upon pulling the guiding catheter 31 out from the living body, the procedure is completed. It should be noted that after the procedure is completed, a very small hole remains on the foramen ovale valve M2 by the pulling-out of the needle portion 1, but it is healed afterward and bad influence such as generation of a thrombus and the like will never occur. Also, even in the region in which the electrode portions 3a, 3a between the atrial septum secundum M1 and the foramen ovale valve M2 are positioned, a very small hole remains by the pulling-out of the electrode portion 3a, 3a, but it is healed afterward and bad influence such as generation of a thrombus and the like will never occur.

Figure 9A:
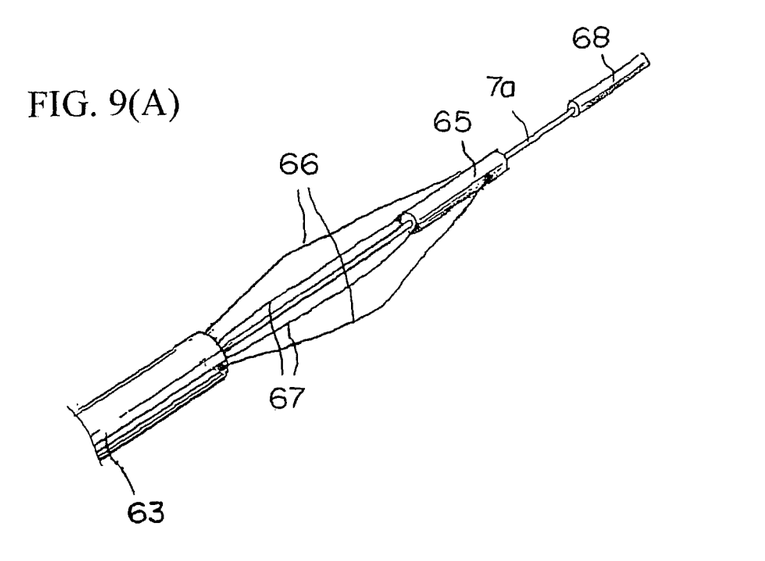
Figure 9B:
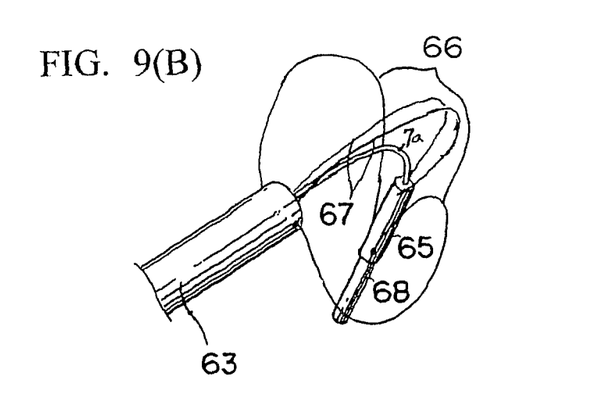

It should be noted that the positioning hold mechanism 60 in the present exemplified embodiment is not limited by the illustrative embodiment mentioned above. For example, FIGS. 9A and 9B are perspective views showing another example of the positioning hold mechanism and, as shown in FIG. 9A, it is also possible to provide the first elastic wire 66 and the second elastic wire 67 between the distal tip sleeve body 65 and the main tube 63 without also providing the middle sleeve body 64 as in the present exemplified embodiment. In this illustrative embodiment, when the main operation rod 7a is moved backward, as shown in FIG. 9B, the second elastic wire 67 is bent and deformed into an arc shape while the first elastic wire 66 is protruded and deformed in an arc shape in the radial direction toward the outside direction. More specifically, the positioning of the stick portion 2 at the center of the foramen ovale O by virtue of the first elastic wire 66 and the holding of the foramen ovale valve M2 by virtue of the contact member 68 and the distal tip sleeve body 65 which are bent by the second elastic wire 67 are to performed simultaneously based on one action caused by the backward movement of the operation member 7a.

The PFO closing device here is not limited only by aforementioned exemplified embodiments and it is possible for a person skilled in the art to employ various modifications within the technical concept of the present invention. In the exemplified embodiment mentioned above, it was explained with respect to a device which is used in a treatment for closing a defect of PFO, but the invention is not limited only by this and it is possible to use it in case of closing a passway-shaped defect such as a left auricle closing device (Left Atrial Appendage) or in case of thermally necrosing a biological tissue in a predetermined region.

With respect to the PFO closing device of the exemplified embodiment, it is merely housed in the catheter and operates a clamper and a cautery device by the operation member, but it is not limited only by this and, for example, it is also possible to carry it until a predetermined position by employing a combination with a so-called catheter having a balloon.

The present invention can be utilized for a device which can close a defect portion of a PFO simply and also safely.

Having described preferred embodiments of the invention with reference to the accompanying drawings, it is to be understood that the invention is not limited to those precise embodiments and that various changes and modifications could be effected therein, and equivalents employed, by one skilled in the art without departing from the spirit or scope of the invention as defined in the appended claims.

What is claimed is:
1. A PFO closing device comprising:
   a catheter having a distal portion, the distal portion of the catheter including first, second, third and fourth separate lumens which are spaced apart from one another;
   a clamper comprised of a needle portion movably positioned in the first lumen at the distal portion of the catheter for piercing a foramen ovale valve and a sandwich member movably positioned in the second lumen at the distal portion of the catheter, the sandwich member and the needle portion together cooperating with one another to sandwich therebetween biological tissue composed of the foramen ovale valve and an atrial septum secundum;
   two electrodes movably positioned in respective ones of the third and fourth lumens at the distal portion of the catheter to project distally beyond a distal end of the catheter, the two electrodes being positionable in the foramen ovale between the foramen ovale valve and the atrial septum secundum;

an electric energy supply unit connected to the two electrodes to supply electric energy to the two electrodes; and the electrodes being insertable into the foramen ovale while the foramen ovale valve and the atrial septum secundum are at the same time sandwiched by the clamper, whereupon electric energy supplied from the electric energy supply unit to the electrodes effects mutual fusing of the foramen ovale valve and the atrial septum secundum.

2. The PFO closing device according to claim 1, wherein the needle portion is comprised of two needle members each possessing a sharply pointed front end.

3. The PFO closing device according to claim 2, wherein the two needle members are connected to a common operation member so that movement of the operation member results in movement of the needle members.

4. The PFO closing device according to claim 1, further comprising a holder portion at the distal portion of the catheter, the first lumen, the second lumen, the third lumen and the fourth lumen passing though the holder portion.

5. The PFO closing device according to claim 1, further comprising an operation lever for moving the two electrodes, the two electrodes being connected to the electric energy supply unit by wires.

6. The PFO closing device according to claim 1, wherein the sandwich member is connected to an operation member so that movement of the operation member results in movement of the sandwich member.

7. The PFO closing device according to claim 1, wherein the needle portion is connected to an operation member so that movement of the operation member results in movement of the needle portion.

8. The PFO closing device according to claim 1, wherein the sandwich member is connected to a first operation member so that movement of the first operation member results in movement of the sandwich member, the needle portion is connected to a second operation member so that movement of the second operation member results in movement of the needle portion, and at least one of the electrodes is connected to a third operation member so that movement of the third operation member results in movement of the at least one electrode.

9. A method for joining together an atrial septum secundum and a foramen ovale valve in a living body to close a patent foramen ovale, the method comprising:

positioning a distal portion of a catheter in a right atrium of the living body, the distal portion of the catheter including first, second, third and fourth separate lumens which are spaced apart from one another, the catheter also comprising: a damper comprised of a needle portion movably positioned in the first lumen at the distal portion of the catheter and a sandwich member movably positioned in the second lumen at the distal portion of the catheter; and two electrodes movably positioned in respective ones of the third and fourth lumens at the distal portion of the catheter to project distally beyond a distal end of the catheter;

piercing the foramen ovale valve with the needle portion;

sandwiching the foramen ovale valve and the atrial septum secundum between the needle portion and the sandwich member;

inserting the two electrodes into the foramen ovale so that the two electrodes are positioned in the foramen ovale while the foramen ovale valve and the atrial septum secundum are at the same time sandwiched between the needle portion and the sandwich member; and supplying electric energy to the two electrodes to effect mutual fusing of the foramen ovale valve and the atrial septum secundum.

10. The method according to claim 9, wherein the needle portion is comprised of two needle members each possessing a sharply pointed front end, and wherein the piercing of the foramen ovale valve with the needle portion comprises piercing the foramen ovale valve with both needle members.

11. The method according to claim 9, wherein the needle portion is connected to an operation member, and wherein the piercing of the foramen ovale valve with the needle portion comprises moving the operation member in a forward direction to move the needle portion in the forward direction to pierce the foramen ovale valve.

12. The method according to claim 9, wherein the sandwiching member is connected to an operation member, and the sandwiching of the foramen ovale valve and the atrial septum secundum between the needle portion and the sandwich member comprises moving the operation member in a rearward direction to cause the sandwiching member to move towards the needle portion.

13. The method according to claim 9, wherein the electrodes are connected to at least one operation member, and the inserting of the two electrodes into the foramen ovale comprises moving the at least one operation member in the forward direction to move the electrodes in the forward direction.

* * * * *